United States Patent
Jun et al.

(10) Patent No.: US 10,779,755 B2
(45) Date of Patent: Sep. 22, 2020

(54) NON-INVASIVE BLOOD SUGAR MEASUREMENT METHOD AND DEVICE USING OPTICAL REFLECTOMETRY

(71) Applicant: DADAM MICRO INC., Seongnam-si Gyeonggi-do (KR)

(72) Inventors: Ik Soo Jun, Cheonan-si (KR); Ki Hong Kim, San Jose, CA (US)

(73) Assignee: DADAM MICRO INC., Seongnam-si, Gyenggi-Do (KR)

( * ) Notice: Subject to any disclaimer, the term of this patent is extended or adjusted under 35 U.S.C. 154(b) by 187 days.

(21) Appl. No.: 16/097,483

(22) PCT Filed: Apr. 24, 2017

(86) PCT No.: PCT/KR2017/004319
§ 371 (c)(1),
(2) Date: Oct. 29, 2018

(87) PCT Pub. No.: WO2017/188675
PCT Pub. Date: Nov. 2, 2017

(65) Prior Publication Data
US 2019/0142312 A1    May 16, 2019

(51) Int. Cl.
*A61B 5/145* (2006.01)
*A61B 5/1455* (2006.01)
(Continued)

(52) U.S. Cl.
CPC ............ *A61B 5/14532* (2013.01); *A61B 5/00* (2013.01); *A61B 5/145* (2013.01); *A61B 5/1455* (2013.01);
(Continued)

(58) Field of Classification Search
CPC . A61B 5/1455; A61B 5/14532; A61B 5/0066; A61B 5/7257
See application file for complete search history.

(56) References Cited

U.S. PATENT DOCUMENTS 6,725,073 B1 *  4/2004  Motamedi .......... A61B 5/14532
                                                           600/316
7,822,452 B2 * 10/2010  Schurman .......... A61B 5/14532
                                                           600/316
(Continued)

FOREIGN PATENT DOCUMENTS

JP    2009-535072 A    10/2009
JP    2010-508056 A     3/2010
(Continued)

*Primary Examiner* — Eric F Winakur
(74) *Attorney, Agent, or Firm* — Novick, Kim & Lee, PLLC; Jae Youn Kim

(57) ABSTRACT

A non-invasive blood sugar measurement device using optical reflectometry is provided. According to an embodiment of the present invention, provided are a specific configuration and method, the configuration comprising: a light generation means for generating light to be emitted at the skin to be measured when OTDR and OFDR are used; an optical measurement means for measuring the intensity of light; an optical system for emitting the generated light at the skin to be measured and transmitting reflected light to the optical measurement means; an analysis means for analyzing collected reflected light on the basis of a change in the intensity of the reflective light with respect to time by using optical reflectometry; and a blood sugar calculation means for calculating, on the basis of the analysis result, a blood sugar level of the skin to be measured.

7 Claims, 2 Drawing Sheets

(51) Int. Cl.
 *A61B 5/00* (2006.01)
 *G01N 33/49* (2006.01)
(52) U.S. Cl.
 CPC ........... *A61B 5/0066* (2013.01); *A61B 5/7257* (2013.01); *G01N 33/49* (2013.01)

(56) References Cited

U.S. PATENT DOCUMENTS

| | | | | |
|---|---|---|---|---|
| 8,036,727 | B2* | 10/2011 | Schurman | A61B 5/1455 |
| | | | | 600/328 |
| 2005/0213103 | A1* | 9/2005 | Everett | A61B 5/0066 |
| | | | | 356/479 |
| 2013/0016360 | A1* | 1/2013 | Ensher | G01B 9/02004 |
| | | | | 356/479 |
| 2015/0168214 | A1* | 6/2015 | Wong | A61B 5/0066 |
| | | | | 356/402 |

FOREIGN PATENT DOCUMENTS

| | | |
|---|---|---|
| JP | 5646337 B2 | 12/2014 |
| JP | 2015-062716 A | 4/2015 |
| KR | 2014-006063 A | 1/2014 |

* cited by examiner

NON-INVASIVE BLOOD SUGAR MEASUREMENT METHOD AND DEVICE USING OPTICAL REFLECTOMETRY

TECHNICAL FIELD

The present invention relates to a non-invasive blood sugar measurement method and device using optical reflectometry and, more particularly, to a non-invasive blood sugar measurement method and device using optical reflectometry, which is used for measuring a glucose concentration in the blood of a human body.

BACKGROUND ART

As the number of patients of diabetes mellitus, which is a modern adult disease, is increasing, there is a need for a portable and easy-to-use blood sugar measurement device for obtaining blood sugar data necessary for the treatment of diabetes. Generally, blood sugar can be grasped by measuring the concentration of glucose contained in blood.

Due to the increase in obesity population caused by the change in modern dietary habits, the number of diabetic patients has been increasing significantly, which has become a social problem. Various ways of maintaining individual healthy living and body have been proposed. In particular, it is recognized that the control of blood sugar is indispensable.

In order to control blood sugar, accurate and easy measurement of blood sugar is required among other things. As blood sugar measurement methods, there have been conventionally proposed a method using a reductive property of glucose, a method using a direct reaction of sugar under acidic conditions, a method using an enzymatic reaction of glucose, and the like. As a clinical medical examination method, there has been used a method in which the blood collected from a finger, a toe or the like or the blood collected by another method is reacted with glucose oxidase, and the degree of coloration using a coloring reaction depending on a glucose concentration in blood is measured and converted into a blood sugar level.

Meanwhile, as methods of measuring a concentration of a body fluid component, particularly a body fluid component such as blood sugar or the like contained in the blood, there are available an invasive method of directly collecting blood to measure a concentration of a specific body fluid component and a non-invasive method (non-blood-collecting method) of measuring a concentration of a specific body fluid component without collecting blood. The invasive method is advantageous in that the measurement reliability is high. However, the invasive method has a problem in that the blood collection using a syringe entails pain, inconvenience and a high risk of infection and a problem in that the use of consumables such as a strip for measurement of a body fluid component, syringe and the like leads to a high economic burden.

In order to solve such a problem, a non-invasive measuring device for measuring body fluid such as blood sugar without blood collection has been proposed. As a non-invasive blood glucose measurement method, there is known a method using an optical measurement method, electric high frequency, impedance, and the like.

In order to solve such a problem, there has been proposed a non-invasive measurement device for measuring a concentration of a body fluid component such as blood sugar or the like without blood collection. As non-invasive blood sugar measurement methods, there are known an optical measurement method, a method using electric high frequency, a method using impedance, and the like.

As optical blood sugar measurement methods, there are known many methods such as a method using spectroscopy, a method using tomography, and the like. Among the most widely used spectroscopy methods, Raman spectroscopy is the most recently attempted spectroscopy. According to the technique for measuring a body fluid component using Raman spectroscopy, light having a specific wavelength is focused on a specific part of a living body such as a capillary or the like, and then a glucose concentration is measured using a Raman spectrum which is wavelength-converted by a glucose molecule.

The method of measuring the body fluid component using the Raman spectroscopy has a disadvantage in that the signal magnitude of Raman spectrum obtained by light irradiation is small. In order to overcome this disadvantage, it may be possible to increase the intensity of the light incident on a human body. However, this may pose a problem in that the increase in the intensity of the light is harmful to the human body and may cause a burn to the human body.

There is also available a method of measuring a blood glucose concentration using a plurality of Raman spectrum signals obtained by irradiating harmless light to the human body at least twice with a time difference left therebetween. However, this method has a problem in that the measurement time is as long as 3 minutes or more.

In addition, a device and method for measuring a blood glucose concentration using optical coherence tomography (OCT) has recently been known. Such a blood glucose measurement technique using the three-dimensional shape called OCT requires a complex, large-sized and costly device for the realization thereof. In addition, the technique makes use of a blood concentrating mechanism for concentrating blood on a measurement portion in order to increase the accuracy of blood glucose concentration measurement. This poses a problem in that the device becomes more complicated and the cost increases dramatically.

SUMMARY

In order to solve the aforementioned problems of the related art, the present invention provides a non-invasive blood sugar measurement method and device using optical reflectometry, which is capable of overcoming the disadvantages of the conventional OCT, such as the complexity, the increase in size and the high cost, and which is high in precision, excellent in reproducibility, inexpensive and small in size.

According to an embodiment of the present invention, there is provided a non-invasive blood sugar measurement device using optical reflectometry, including: a light generation means for generating light to be irradiated on a measurement target skin; an optical measurement means for measuring the intensity of light; an optical system for irradiating the light generated by the light generation means on the measurement target skin and transmitting reflected or scattered light to the optical measurement means; an analysis means for analyzing the reflected light collected by optical reflectometry in terms of a change rate in the intensity of light with respect to time; and a blood sugar level calculation means for calculating a blood sugar level in the measurement target skin based on a result of the analysis means.

According to another embodiment of the present invention, there is provided a non-invasive blood sugar measurement method using optical reflectometry, including: a light generation step of generating light to be irradiated on a measurement target skin; an optical measurement step of measuring the intensity of light; an optical processing step of irradiating the light generated in the light generation step on the measurement target skin and transmitting reflected or interfered light from the skin to the optical measurement step; a light analysis step of analyzing the collected reflected light in terms of a change rate in the intensity of light with respect to time; and a blood sugar level calculation step of calculating a blood sugar level in the measurement target skin based on a result of the light analysis step.

The following two embodiments are provided as the non-invasive blood sugar measurement device and method using optical reflectometry.

As one embodiment, when the optical reflectometry is composed of optical time domain reflectometry (OTDR), the light generation means is a light pulse generator for generating light having a single wavelength, the optical system is a light transmission path for transmitting the reflected light to the measurement target skin and transmitting the reflected light from the measurement target skin to a light collector, the analysis means is configured to calculate a change rate of the intensity of light for the depth of the measurement target skin from the intensity of light according to the time, and the blood sugar level calculation means is configured to calculate a blood sugar level based on a result of the analysis means using an equation:

blood sugar level (mg/dl)=$k \times (Du/Dt) + C0$ where dU/dt is a light intensity change rate according to a skin depth (t) of an inner skin layer of interest, k is a coefficient for a (central) wavelength of irradiated light, and C0 is a blood sugar level when the light intensity change rate is zero.

As another embodiment, when the optical reflectometry is composed of optical frequency domain reflectometry (OFDR), the light generation means is a wavelength-variable light source including a wavelength-variable laser diode (LD) that makes the intensity of light uniform and outputs coherent light by varying the wavelength of light around a specific wavelength, the optical system is composed of an interferometer for causing reference light to interfere with the reflected light, the optical measurement means is configured to measure the intensity of interfered light, the analysis means is configured to calculate the intensity of light collected for each frequency according to the wavelength change of the irradiated light an calculate a change rate of the intensity of light for each depth of the measurement target skin by converting the intensity of light through inverse Fourier transformation using discrete Fourier transformation (DFT), and the blood sugar level calculation means is configured to calculate a blood sugar level as in the embodiment of the OTDR configuration.

As a further embodiment in which the optical reflectometry is composed of optical frequency domain reflectometry (OFDR), a low coherent light source or a wide band light source is used as the light irradiation means, the optical system is formed of an interferometer for causing reflected light and reference light to interfere with each other, the optical measurement means may simultaneously measure the frequency-by-frequency intensity of the low coherent interference (LCI) light and the wide band interference (WBI) light passed through the interferometer through the use of the interferometer, the spectrometer is formed by combining a spectroscopic means such as a diffraction grating (DG) or the like and a stripe detector, a CCD (Charge Coupled Device), a PDA (Photo Diode Array) or the like is used as the stripe detector, the analysis means calculates the intensity of light collected for each frequency and calculates a rate of change of light intensity for each depth of a measurement target skin through inverse Fourier transformation using discrete Fourier transformation (DFT), and the blood sugar level calculation means calculates a blood sugar level as in the embodiment of the OTDR configuration.

The non-invasive blood sugar measurement device using optical reflectometry according to an embodiment of the present invention can easily analyze and extract a concentration of a body fluid component such as blood sugar or the like with enhanced convenience and reproducibility while making it possible to measure to a concentration of a body fluid component in most parts of a human skin and can enjoy improved portability and reduced size.

DETAILED DESCRIPTION

Figure 1:
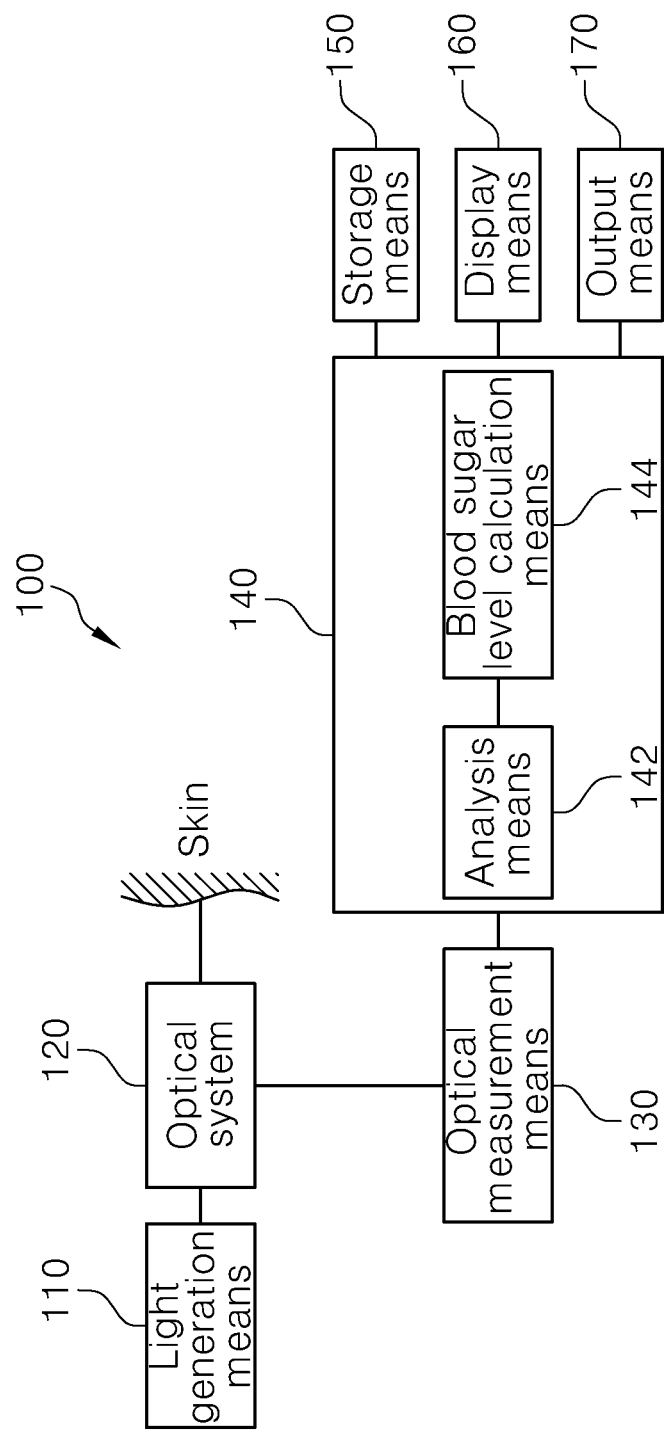
FIG. 1 is a block diagram of a non-invasive blood sugar measurement device using optical reflectometry according to an embodiment of the present invention.

Hereinafter, preferred embodiments of the present invention will be described in detail with reference to the accompanying drawings. The embodiments of the present invention may be modified in various forms. The scope of the present invention should not be construed as being limited to the embodiments described below. These embodiments are provided to specifically explain the present invention to those skilled in the art. Thus, the shape of each element shown in the drawings may be exaggerated to emphasize a clearer description.

The terms "first", "second" and the like may be used to describe various elements. However, the elements should not be limited by these terms. The terms are used only for the purpose of distinguishing one component from another.

The terms referred to herein are used merely for the purpose of describing particular embodiments and are not intended to limit the present invention. A singular form includes a plural form unless the context clearly dictates otherwise. In this application, the terms "include", "have" and the like are used to specify the existence of a feature, a figure, a step, an operation, an element, a part or a combination thereof described in the specification and are not intended to exclude the existence or the possibility of addition of one or more other features, figures, steps, operations, components, parts, or combinations thereof.

FIG. 1 is a block diagram of a non-invasive blood sugar measurement device using optical reflectometry according to an embodiment of the present invention.

Hereinafter, a non-invasive blood sugar measurement device using optical reflectometry according to an embodiment of the present invention will be described in detail with reference to the drawings.

The non-invasive blood sugar measurement device 100 using optical reflectometry according to an embodiment of the present invention includes a light generation means 110, an optical system 120, an optical measurement means 130, a control means 140, a storage means 150, a display means 160, and an output means 170. The control means 140 includes an analysis means 142 and a blood sugar level calculation means 144.

The non-invasive blood sugar measurement device 100 makes use of optical reflectometry. In the optical reflectometry, basic optical time domain reflectometry (hereinafter referred to as OTDR) has been widely used for industrial applications along with the development of optical communication technology for the purpose of accurately measuring an abnormal position and an abnormal personality in an optical path (an optical fiber or the like) by continuously measuring and storing the intensity of reflected light during the reflection time based on the reflected light (Fresnel reflected light and Rayleigh scattered light) generated when the irradiation light having a pulse form propagates through an optical path and by analyzing and presenting the change in the intensity of the reflected light as a function of time.

Furthermore, in the optical reflectometry, optical frequency domain reflectometry (hereinafter referred to as OFDR) is a method which presents a result of analyzing a change in the intensity of reflected light as a time function just like the OTDR. In the OFDR, instead of optical pulses, a wavelength-variable light source having a stable amplitude and a wavelength varying around a certain frequency is used as a light source. A change in the reflection coefficient of each wavelength is measured and stored. Then, the change in the reflection coefficient is converted into a time function through discrete Fourier transformation (hereinafter referred to as DFT). The subsequent process is the same as the OTDR. The OFDR is superior to the OTDR in resolution and is recently used to more accurately grasp the internal characteristics of an optical element.

In another embodiment where the optical reflectometry is composed of optical frequency domain reflectometry (OFDR), a low coherent light source or a wide band light source is used as the light irradiation means. The optical system is formed of an interferometer for causing reflected light and reference light to interfere with each other. The optical measurement means may simultaneously measure the frequency-by-frequency intensity of the low coherent interference (LCI) light and the wide band interference (WBI) light passed through the interferometer through the use of the interferometer. The spectrometer may be formed by combining a spectroscopic means such as a diffraction grating (DG) or the like and a stripe detector. A CCD (Charge Coupled Device), a PDA (Photo Diode Array) or a CMOS may be used as the stripe detector. The analysis means calculates the intensity of light collected for each frequency and calculates a rate of change of light intensity for each depth of a measurement target skin through inverse Fourier transformation using discrete Fourier transformation (DFT). The blood sugar level calculation means may calculate a blood sugar level as in the embodiment of the OTDR configuration.

The non-invasive blood sugar measurement device 100 optical reflectometry according to the embodiment of the present invention may use either the OTDR or the OFDR in the optical reflectometry described above. In the final analysis process, both the OTDR and the OFDR commonly uses a blood sugar level extraction method that tracks a change in the intensity of reflected light with respect to time, analyzes the reflectance distribution to the skin depth from the change in the intensity of reflected light and calculates a blood sugar level from the reflectance distribution.

The configuration, operation principle and blood sugar level calculation principle of the non-invasive blood sugar measurement device 100 using OTDR as basic optical reflectometry will be described as an embodiment.

In the OTDR, the light generation means 110 is an light pulse generator for generating pulse light of a single wavelength.

The optical system 120 may be optically connected so as to irradiate the light generated by the light generation means 110 to a measurement target skin and measure the reflected light from the skin using the optical measurement means 130.

The optical measurement means 130 receives the light reflected or scattered by the measurement target skin through the optical system 120 and measures the intensity of the light. For example, the optical measurement means 130 may be a photo detector (hereinafter referred to as PD).

The control means 140 may control the calculation, storage and output of the blood sugar level calculated according to the intensity of the light collected by the optical measurement means 130 and also may control the analysis means 142 and the blood sugar level calculation means 144.

The analysis means 142 may analyze a rate of change of the intensity of the light collected over time using the optical reflectometry.

The storage means 150 may store an intermediate analysis result of the analysis means 142, a calculation result of the blood sugar level calculation means 144, reference values, statistical values, and the like.

The display means 160 may display the intermediate analysis result of the analysis means 142, the operation result of the blood sugar level calculation means 144 and the calculated blood sugar level.

The output means 170 may output the blood sugar level calculated by the blood sugar level calculation means 144.

That is, in order for the non-invasive blood sugar measurement device 100 to measure the blood sugar level using a technique of comparison of reflection coefficient of scattered light for each depth (position) of a skin, the analysis means 142 may measure a change rate of the light intensity for each depth of a measurement target skin through the intensity of the collected light according to the time.

The blood sugar level calculation means 144 may calculate the blood sugar level for a specific depth of the measurement target skin based on the time difference of the intensity of the collected light or the change rate of the intensity of light with respect to time.

Hereinafter, the operation principle of the non-invasive blood sugar measurement device 100 using the OTDR according to the embodiment of the present invention will be described with reference to FIG. 2.

The OTDR is a technique of measuring a reflectance coefficient for each distance (depth) by irradiating a short light pulse on an inspection target object as a measurement target (an optical fiber or a skin in the case of the present invention), measuring the reflection time of the pulse and measuring the intensity of a reflected wave over time.

In this regard, the basic principle of the OTDR is that, if a short light pulse is irradiated on a measurement target skin, the light travels in the depth direction of the skin at a velocity v as shown in equation (1):

$$V = c/n_{eff} \qquad (1)$$

where c is the velocity of light in vacuum, and $n_{eff}$ is the effective refractive index in the skin.

Figure 2:
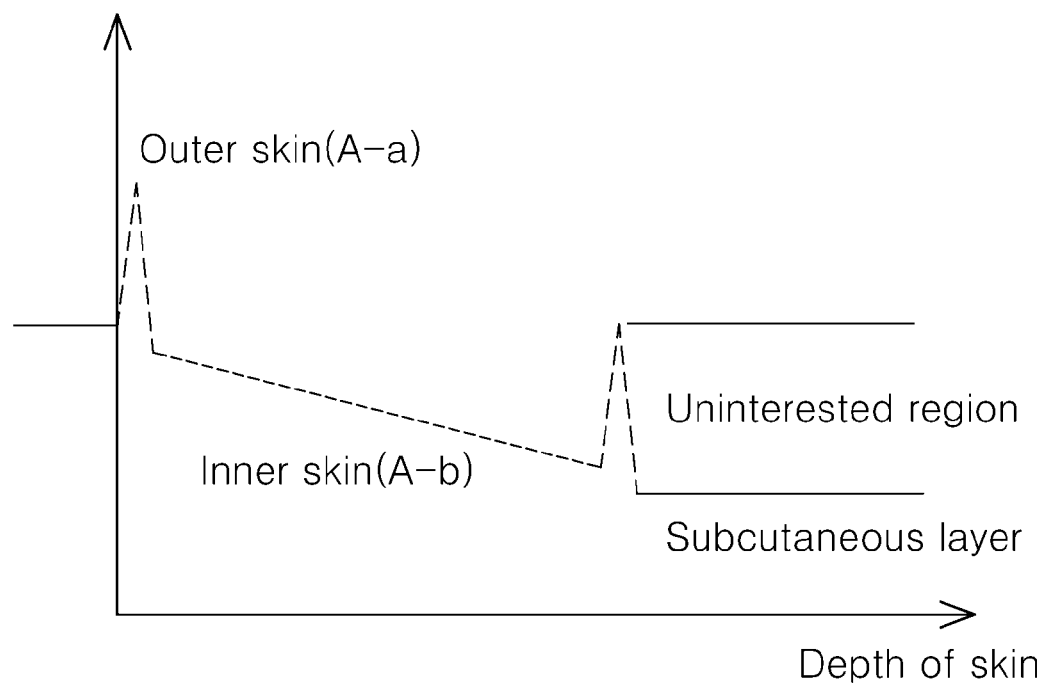
FIG. 2 is a graph showing a change in the intensity of reflected light according to the depth of a skin in the non-invasive blood sugar measurement device using optical reflectometry according to an embodiment of the present invention.

At this time, as the light travels, the light continues to form a reflected partly at a reflection interface (for example, (A-a) in FIG. 2) while passing through the inner skin. This is due to the random scattering caused by the difference in refractive index coefficient between red blood cells and blood.

Since the difference in refractive index coefficient bet red blood cells and blood varies depending on the blood sugar level, the change amount (slope) of the reflection coefficient in the inner skin is also different.

The following relationship exists between the reflectance at a specific interface and the refractive index of a medium before and after the interface:

$$r=[(n_1-n_2)/(n_1+n_2)]^2$$

where r is the reflectance at the interface, $n_1$ is the refractive index of the medium before the light enters the interface, and $n_2$ is the refractive index of the medium after the light enters the interface.

The changes of refractive indexes $n_1$, $n_2$, $n_3$ . . . of the medium before and after the interface with respect to the light traveling along the depth are indicated by the reflectance $r_1$, $r_2$, $r_3$ . . . at the respective interfaces.

That is, the reflectance of light at the reflective interface has a predetermined relationship with the difference between the refractive indices of the media on both sides of the interface. Therefore, the change in the refractive index appears as a change in the reflectance at each interface.

As a result, the intensity of reflected light indicates a specific slope value (unique value) as shown by (A-b) in FIG. 2. At this time, the glucose level in the blood can be calculated by calculating the difference in the slope.

In the case of using a technique of comparing the reflectance of the skin for each depth by measuring the time-dependent intensity of the reflected light for the random scattering light in this manner, the glucose concentration in the blood of the human body, i.e., the blood sugar level can be measured by comparing and analyzing the difference between the reflectance and the scattering in the skin of the human body, specifically the horny layer, the inner layer and the subcutaneous fat layer of the skin.

FIG. 2 is a graph showing a change in the intensity of reflected light depending on the depth of a skin in the non-invasive blood sugar measurement device using optical reflectometry according to the embodiment of the present invention. As shown in FIG. 2, according to the relation of the reflection coefficient obtained by optical reflectometry to the time axis, it can be noted that steep reflection (A-a) occurs in the outer layer of the skin and gently distributed reflection (A-b) occurs in the inner layer of the skin. There may be a specific reflection phenomenon near the subcutaneous fat layer. In the present invention, the glucose level in the blood can be calculated by calculating the slope of the distributed reflection (A-b).

As described above, the blood sugar level can be calculated by plotting the intensity of light with respect to the irradiation depth in the outer layer and the inner layer of the skin and analyzing the slope thereof. That is, as the slope increases, the glucose level decreases. On the contrary, as the slope decreases, the glucose level increases.

In this regard, the blood sugar level calculation means 144 analyzes the change in the intensity of the reflected light with respect to the time. When the linear relationship is below the clinical value error range, the blood sugar level can be calculated by the following equation (2) using a technique of comparing the reflection coefficient for each skin depth:

$$\text{blood sugar level (mg/dl)} = k \times (dU/dt) + C0 \qquad (2)$$

where dU/dt is the light intensity change rate according to the skin depth (t) of the inner layer of interest, k is the coefficient for the (central) wavelength of the irradiated light, and C0 is the blood sugar level when the light intensity change rate is zero.

Meanwhile, the equation varies depending on the wavelength because the refractive index depends on the wavelength of glucose, blood and skin. However, when the same wavelength is used, a functional relationship between the slope and glucose can be obtained and the equation can be consistently derived.

In equation (2), k is a coefficient according to wavelength. Since the reaction depends on the wavelength of blood or red blood cells, it is necessary to obtain an absolute k value. For this purpose, the calibration of the absolute value is attempted using two or more wavelengths. This may limit the number of wavelengths to one (1) (i.e., use of a light source having one wavelength) when stable statistical values are obtained according to the clinical result of a k value.

In one embodiment, when the non-invasive blood sugar measurement device 100 measures a blood sugar level using OFDR, the light generation means 110 is a wavelength-variable light source that outputs light by varying the wavelength thereof.

In this regard, a wavelength-variable laser diode or a wavelength multiplexer such as a prism or a filter may be used as the wavelength-variable light source. The wavelength-variable light source is preferably a wavelength-variable laser diode having excellent coherence. For example, the wavelength-variable laser diode sweeps the laser light having a frequency of 200 to 300 THz and a wavelength of 1.30 to 1.55 μm by ±100 ppm (i.e., ±200 GHz or 300 GHz).

The optical system 120 may be formed of an interferometer that causes reflected light to interfere with reference light. The distance resolution may be dramatically increased by constructing the optical system 120 using a fiber type or free space type interferometer including a Mach-Zehnder interferometer and a Michelson interferometer. Such OFDR is more appropriate than OTDR when measuring the reflection characteristic of a fine polymer such as blood sugar or the like in a skin (inner skin) that requires a highly precise distance resolution at a short distance (depth) of several millimeters.

The optical measurement means 130 may be formed of a PD.

The analysis means 142 may calculate the intensity of the light collected for each frequency according to the wavelength of the irradiated light using the OFDR and may calculates the change rate of the light intensity according to the depth of the measurement target skin as in the OTDR through the inverse Fourier transformation.

The blood sugar level calculation means 144 measures the reflection time of the scattered light so that when the linear relationship is below the clinical value error range, the blood sugar level can be calculated by equation (2) using a technique of comparison of reflection coefficients for skin depth as in the OTDR.

More specifically, the principle of the embodiment of the non-invasive blood sugar measurement device using OFDR will be described. The light intensity of the light generation means 110 is stabilized at a constant amplitude of $a_0(t)$. Instead, the wavelength may be varied to $v0+(\gamma/2)t$ by using a wavelength-variable element to generate light as shown in equation (3):

$$a_0(t) = |a_0|e^{-j2\pi[v_0+(\frac{\gamma}{2})t]t} \quad (3)$$

where $0 \leq t \leq T$, $a_0$ is the amplitude of light, and y is the frequency sweeping rate.

At this time, the characteristic according to the reflection coefficient for each frequency (wavelength) appearing in the optical measurement means 130 is represented by equation (4):

$$\tilde{U}_{PD}(v) \triangleq 2U_0 \Sigma_{m=1}^{M} |r_{meff}| \cos(2\pi v\tau_m + \epsilon_m) \quad (4)$$

where $\tilde{U}_{PD}(v)$ is the interference light emitted through the optical interferometer at the time when the light frequency is u (only the beating portion excluding the DC portion of $U_{PD}$ is shown), $U_0$ is a constant according to the intensity of reflected light and the photosensitivity characteristic ($\alpha$) of a light receiving element (i.e., $U_0 = \alpha|\alpha_0|^2$), rmeff is the effective reflection coefficient of the $m^{th}$ reflector, $\tau_m$ is a difference between the time delay of the light reflected from the $m^{th}$ reflector and the time delay of the reference wave of the reference light, and εm is a phase constant according to an individual reflector.

$\tilde{U}_{PD}(v)$ is subjected to inverse Fourier transformation by DFT using equation (5):

$$F(\tau) = \int_{v_0-(\Delta v/2)}^{v_0+(\Delta v/2)} U_{PD}(v) e^{j2\pi v\tau} dv \quad (5)$$

where $F(\tau)$ is a reflection function in a time ($\tau$) region and a time function of the light intensity observed regardless of the temporal variation frequency (v) and the phase ($\epsilon$) which are light wave characteristic parameters.

As a result of equation (5), the characteristics of the light wave related to the frequency (v) and phase ($\epsilon$) in the frequency domain are converted into the light intensity characteristics in the time domain. Using this conversion, the glucose level as a blood sugar level can be calculated in the same manner as in OTDR.

The time or distance (depth) resolution of the reflected light intensity characteristics appearing in the time domain is represented by equation (6):

$$Z = (\Delta\tau)(c/2n) = c/(2n\Delta v) \quad (6)$$

where c is the velocity of light in vacuum, $v = v_{max} - v_{min}$, and n is the refractive index.

By using OFDR in the non-invasive blood sugar measurement device using optical reflectometry as described above, as compared with the case where OTDR is used, it is possible to drastically improve the distance (depth) resolution at a short distance where the coherence of light is maintained. This is suitable for the purpose of the present invention in which a blood sugar level is measured in the inner skin layer of several millimeters or less in depth.

While the present invention has been described with reference to the preferred embodiment, this description is intended to enhance the understanding of the technical contents of the present invention and is not intended to limit the technical scope of the present invention.

It will be apparent to those skilled in the art that various modifications and variations can be made without departing from the spirit and scope of the invention. Needless to say, such modifications and variations fall within the technical scope of the present invention as defined by the appended claims.

What is claimed is:

1. A non-invasive blood sugar measurement device using optical reflectometry, comprising:
   a light generation means for generating light to be irradiated on a measurement target skin;
   an optical system for irradiating the light generated by the light generation means on the measurement target skin and transmitting reflected light to an optical measurement means configured to measure an intensity of the reflected light;
   an analysis means for analyzing the reflected light collected by using the optical reflectometry in terms of a change rate in the intensity of the reflected light with respect to time; and
   a blood sugar level calculation means for calculating a blood sugar level in the measurement target skin based on the analyzing of the reflected light,
   wherein the optical reflectometry is optical frequency domain reflectometry (OFDR), the light generation means is a wavelength-variable light source, the optical system is an interferometer for causing reference light to interfere with the reflected light, the optical measurement means is a photo detector (PD), and the analysis means is configured to analyze the change rate of the intensity of the reflected light for a depth of the measurement target skin by converting the intensity of the reflected light collected for each light frequency according to a wavelength of the irradiated light into a time domain through inverse Fourier transformation.

2. The device of claim 1, wherein the wavelength-variable light source as the light generation means is composed of a wavelength-variable laser diode for varying a frequency around a specific frequency.

3. The device of claim 1, wherein the interferometer used as the optical system is configured to use an optical fiber or a free space as a light path and is composed of one of a Mach-Zehnder interferometer and a Michelson interferometer.

4. The device of claim 1, wherein the blood sugar level is calculated by the following equation:

blood sugar level (mg/dl)=$k \times (dU/dt) + C0$ wherein dU/dt is a light intensity change rate according to a skin depth (t) of an inner skin layer of the measurement target skin, k is a coefficient for a central wavelength of the irradiated light, and C0 is a blood sugar level when the light intensity change rate is zero.

5. A non-invasive blood sugar measurement method which makes use of the non-invasive blood sugar measurement device using the optical reflectometry of claim 1, comprising:
   a light generation step of generating light to be irradiated on the measurement target skin;
   an optical processing step of irradiating the light generated in the light generation step on the measurement target skin and transmitting reflected or interfered light from the skin to an optical measurement step;
   an optical measurement step of measuring an intensity of the reflected light;
   a light analysis step of analyzing the reflected light in terms of a change rate in the intensity of the reflected light with respect to time; and
   a blood sugar level calculation step of calculating a blood sugar level in the measurement target skin based on a result of the light analysis step,
   wherein the blood sugar level is calculated by the following equation:

blood sugar level (mg/dl)=$k \times (dU/dt) + C0$ wherein dU/dt is a light intensity change rate according to a skin depth (t) of an inner skin layer of the measurement target skin, k is a coefficient for a central wavelength of the irradiated light, and C0 is a blood sugar level when the light intensity change rate is zero.

6. A non-invasive blood sugar measurement device using optical reflectometry, comprising:
- a light generation means for generating light to be irradiated on a measurement target skin;
- an optical system for irradiating the light generated by the light generation means on the measurement target skin and transmitting reflected light to an optical measurement means configured to measure an intensity of the reflected light;
- an analysis means for analyzing the reflected light collected by using the optical reflectometry in terms of a change rate in the intensity of the reflected light with respect to time; and
- a blood sugar level calculation means for calculating a blood sugar level in the measurement target skin based on the analyzing of the reflected light,
- wherein the optical reflectometry is optical frequency domain reflectometry (OFDR), the light generation means is a low coherent light source or a wide band light source, the optical system is an interferometer for causing reference light to interfere with the reflected light, the optical measurement means is configured to simultaneously measure the intensity of the reflected light for a frequency with a spectrometer as a combination of a spectroscopic means including a diffraction grating and a stripe detector, and the analysis means is configured to calculate the intensity of the reflected light measured for the frequency and calculate a change rate of the intensity of the reflected light for a depth of the measurement target skin through inverse Fourier transformation using discrete Fourier transformation (DFT).

7. A non-invasive blood sugar measurement device using optical reflectometry, comprising:
- a light generation means for generating light to be irradiated on a measurement target skin;
- an optical system for irradiating the light generated by the light generation means on the measurement target skin and transmitting reflected light to an optical measurement means configured to measure an intensity of the reflected light;
- an analysis means for analyzing the reflected light collected by using the optical reflectometry in terms of a change rate in the intensity of the reflected light with respect to time; and
- a blood sugar level calculation means for calculating a blood sugar level in the measurement target skin based on the analyzing of the reflected light ,
- wherein the optical reflectometry is optical time domain reflectometry (OTDR), the light generation means is a light pulse generator for generating light having a single wavelength, the optical system is composed of a combination of an optical fiber and an optical element, the optical measurement means is a photo detector (PD) for measuring the intensity of the reflected light transmitted by the optical system, and the analysis means is configured to analyze the change rate of the intensity of the reflected light for a depth of the measurement target skin from the intensity of the reflected light.

* * * * *